(12) United States Patent
Campagna

(10) Patent No.: US 7,996,095 B2
(45) Date of Patent: Aug. 9, 2011

(54) METHOD AND ARRANGEMENT FOR CONTROLLING A MAGNETIC RESONANCE TOMOGRAPHY APPARATUS

(75) Inventor: Swen Campagna, Engelthal (DE)

(73) Assignee: Siemens Aktiengesellschaft, Munich (DE)

( * ) Notice: Subject to any disclaimer, the term of this patent is extended or adjusted under 35 U.S.C. 154(b) by 425 days.

(21) Appl. No.: 11/934,199

(22) Filed: Nov. 2, 2007

(65) Prior Publication Data

US 2008/0108891 A1    May 8, 2008

(30) Foreign Application Priority Data

Nov. 6, 2006  (DE) .......................... 10 2006 052 223

(51) Int. Cl.
*G05B 13/02* (2006.01)
*G06G 7/48* (2006.01)
*G01V 3/00* (2006.01)

(52) U.S. Cl. ............... 700/29; 703/6; 382/131; 324/307

(58) Field of Classification Search .............. 700/29, 700/52, 19, 21, 266–274; 706/924; 703/6, 703/7; 324/307; 382/131
See application file for complete search history.

(56) References Cited

U.S. PATENT DOCUMENTS

| | | | |
|---|---|---|---|
| 6,035,328 A | 3/2000 | Soukal | |
| 6,126,450 A * | 10/2000 | Mukai et al. | 434/262 |
| 7,099,721 B2 * | 8/2006 | Dunnill et al. | 700/73 |
| 7,598,737 B2 * | 10/2009 | Campagna | 324/307 |
| 7,613,672 B2 * | 11/2009 | West et al. | 706/48 |
| 2006/0153436 A1 * | 7/2006 | Haras | 382/131 |

FOREIGN PATENT DOCUMENTS

DE    10 2004 039 680 A1    11/2005

* cited by examiner

*Primary Examiner* — Albert Decady
*Assistant Examiner* — Sivalingam Sivanesan
(74) *Attorney, Agent, or Firm* — Schiff Hardin LLP

(57) ABSTRACT

In a method, system, and a computer-readable medium being a data structure for remote control of an MR scanner for execution of a corresponding measurement, all method steps for controlling or for preparation of the MR scanner are executed on a controller that is independent of the real scanner. A virtual apparatus that simulates the real scanner is implemented on the controller. Control parameters that are relayed to the scanner from the controller in order to prepare the scanner for a measurement are generated from the automatically-registered parameters.

8 Claims, 1 Drawing Sheet

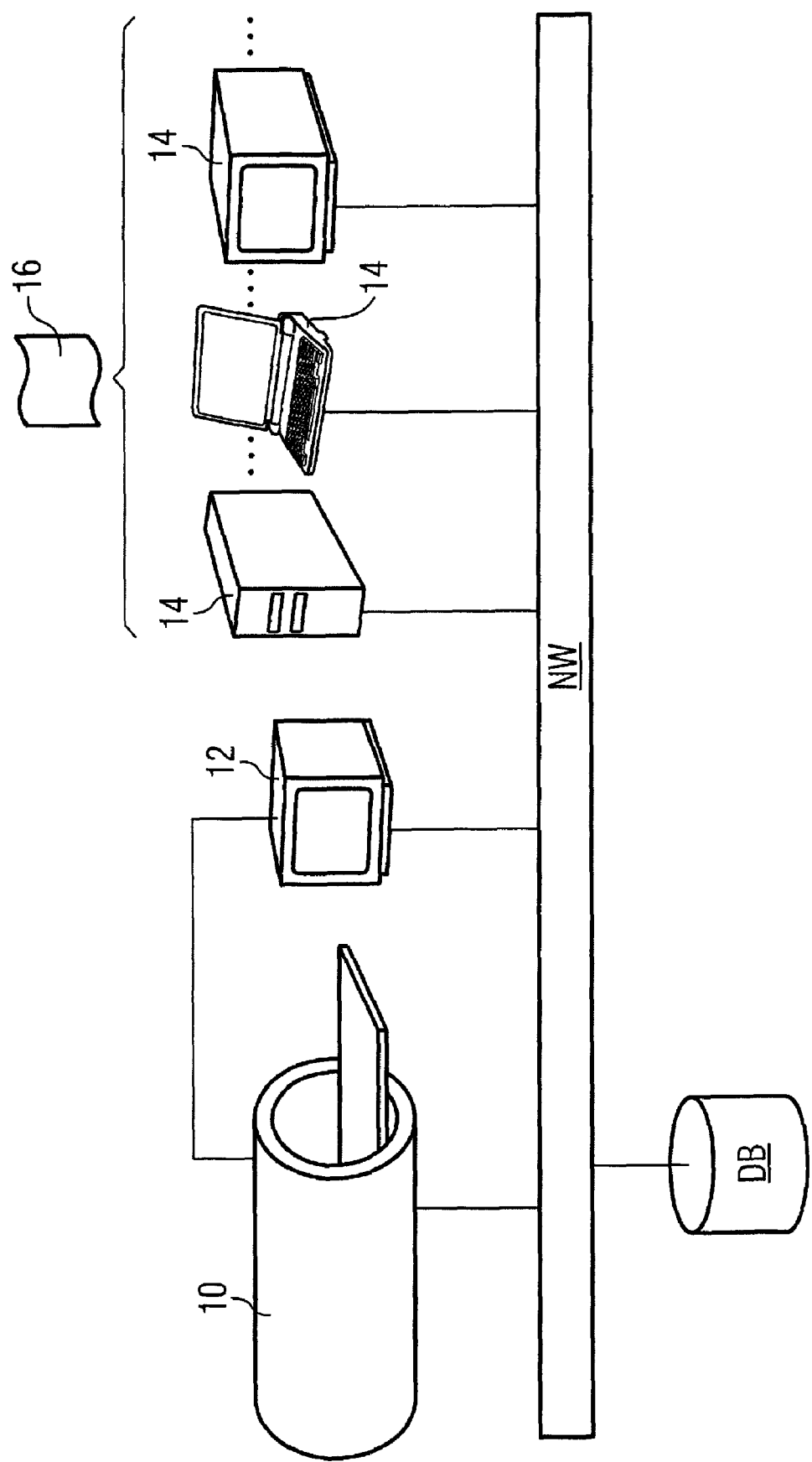

METHOD AND ARRANGEMENT FOR CONTROLLING A MAGNETIC RESONANCE TOMOGRAPHY APPARATUS

BACKGROUND OF THE INVENTION

1. Field of the Invention

The present invention concerns medical technology and data processing and in particular in the area of controlling magnetic resonance tomography systems or other medical data acquisition apparatuses.

2. Description of the Prior Art

The invention in particular concerns a method, a system, and a computer-readable storage medium encoded with a data structure for controlling a medical measurement apparatus such as, for example, a magnetic resonance tomography system or another tomography system.

When an examination is to be executed at a complex medical system such as, for example, an imaging system such as a magnetic resonance tomography system, it is necessary for the examination system or the examination apparatus to be prepared for the respective examination. This typically ensues via an operator console through which a number of parameters are set. The parameters are dependent on the respective examination apparatus (they are measurement apparatus-specific parameters), on the respective examination (which organ should be examined?) and possibly on further general parameters (for example which specific apparatus type, which equipment exists, patient-dependent parameters and possibly even parameters that are dependent on the respective sequence of the planned and/or already-occurred measurements). For example, for a specific examination it can be necessary that further surface coils, further injectors or other modules (such as, for example, EKG sensors) must be provided.

Overall it is necessary that a number of configurations and settings must be made on the apparatus as preparation measures. The preparation measures are dependent on the ability of the machine to ultimately process or execute the measurement (for example coil type, number of the coils, scanner software etc.). These measurement apparatus-specific parameters must be taken into account in the preparation.

There are different points of view as to where and when these preparation measures must or can be executed.

It was previously necessary to execute the preparation measures manually at the apparatus itself. The execution of the preparation measures at the measurement apparatus itself was therefore necessary in order to be able to prepare the respective measurement apparatus-specific control variables for the application case.

Operator consoles for imaging medical examination systems are known from DE 10 2004 039 680 A1, that allow the operating interface for the medical examination system to be relocated to the operator console and the operator console is connected with the medical examination systems via a local network. A temporal decoupling of the input of measurement protocol parameters from the actual measurement procedure via the medical examination systems and the implementation of a virtual machine are, however, not provided in DE 10 2004 039 680 A1.

The preparation measures are very closely coupled with the actual measurement procedure or the respective measurement apparatus. In the previous preparation measures according to the prior art it was therefore frequently necessary to execute the preparation measures immediately in time before the actual measurement, but this disadvantageously limits the flexibility in an examination.

In order to be able to already temporally bring forward specific preparation measures, the use of an "auto-align mechanism" for magnetic resonance tomographs is known, in which a slice positioning is selected based on a reference image, the slice positioning then later being adapted to the current protocol in the actual examination (measurement) by the apparatus. With regard to the preparation measures for the coils, it is known to automatically display in a user (via software) the coils that are currently connected to the respective apparatus. Since a number of further preparation measures are still necessary in addition to the configuration of the coils, the previous known mechanisms of the prior art are merely individual measures that have only a local importance and are overall of limited use.

An improvement in the preparation measures is therefore important, not the least since the apparatuses are very expensive-intensive and normally very heavily used apparatuses. If preparation measures are executed at the apparatus itself, the effective utilization of the apparatus (for a measurement) inevitably therewith decreases.

Moreover, the point in time for the preparation measures has conventionally been very limited, which disadvantageously restricted the flexibility in clinical everyday use. Furthermore, the risk exists that incorrect settings are made due to the manual preparation, perhaps because the current technical equipment of the tomography system was not entirely or correctly comprehended.

SUMMARY OF THE INVENTION

An object of the present invention is to provide a method with which the preparation and control of a medical technology measurement apparatus can be improved and in particular simplified, automated and be made location, independent or machine-independent.

This object is also achieved in accordance with the invention by a system, and a computer-readable medium encoded with a data structure.

In the following the invention is described in the context of the method. Features or alternative aspects that are mentioned are likewise applicable to the system and the storage medium.

In the inventive method for controlling a medical apparatus (in particular an imaging measurement apparatus such as, for example, a magnetic resonance tomography system) for data acquisition apparatus-specific parameters and/or measurement-specific parameters are registered, control parameters are generated in an electronic controller using the registered parameters for the purpose of controlling the medical apparatus, and apparatus is indirectly controlled with the control parameters generated by the controller, with the controller being independent of the medical apparatus to be controlled, by implementing an abstract virtual apparatus with the controller, this abstract virtual apparatus simulating the medical apparatus to be controlled by the virtual apparatus providing the same functionality as the medical apparatus.

The control encompasses all measures for preparation and/or for activation or execution of a measurement task for a complex medical measurement system or measurement apparatus. This includes all steps that must necessarily be executed before or during the actual measurement process(es). These are executed without user interaction and in particular concern a setting, a configuration, a selection of a number of different parameters (for example position settings for the patient positioning, selection of surface coils etc.).

The apparatus is typically a medical measurement apparatus such as, for example, a magnetic resonance tomography apparatus. However, the concept of the invention is not limited to this apparatus type but also can be applied to other apparatus types such as, for example, computed tomograph systems, x-ray apparatuses or further laboratory apparatuses. The apparatus typically serves for implementation of a measurement on a patient.

The term "registration of parameters" as used herein encompasses a manual registration (by appropriate user input via a user interface), an importation, an automatic registration (by importation of corresponding data sets), a local registration by a local access, or a remote registration by access over a network.

The apparatus-specific parameters are data that have a relation to the respective measurement apparatus. They are normally system-specific and/or individual to the apparatus, such as (for example): the number of shim channels, type and number of radio-frequency reception channels, slew rate and maximum gradient strength, surface coils, injectors, etc. Another example of apparatus-specific parameters is data that are related to the system in which the respective apparatus is integrated and thus concern variables such as storage space, transfer capacity, performance, etc.

The measurement-specific parameters are data that have a relation to the planned measurement or, respectively, the measurement to be controlled. These include data that concern questions such as: which organ should be measured, which degree of detail should the measurement have, etc.

The control parameters serve for controlling the respective apparatus and are generated automatically using the registered apparatus-specific parameters and/or using the measurement-specific parameters.

The electronic controller for controlling the apparatus has a user interface and an interface to the respective apparatus to be controlled. The controller can be a computer, portion of a data processor, a standalone system, a network system, a laptop, a PDA or another mobile or stationary apparatus.

According to a further aspect of the invention, the controller for controlling the apparatus is independent of the apparatus to be controlled itself. That means that the controller can be fashioned entirely decoupled from the apparatus to be controlled i.e., separate from the apparatus to be controlled. The controller is typically not itself the apparatus to be controlled or a module associated therewith (such as, for example, an operator console). According to the invention, the apparatus thus does not have to be controlled via the operator console of the respective apparatus but rather can be controlled externally from an arbitrary controller. This brings an enormous growth in flexibility and moreover also leads to a performance increase via better utilization of the measurement apparatus. Moreover, a remote control of the measurement apparatus is possible since the control can ensue from a remote device). The control data are then transferred to the apparatus either via a network or via another interface (for example storage media such as USB stick, memory card, etc.)

According to one aspect of the invention, the method proceeds with access to an inventory databank. Data that identify with which inventory the respective measurement apparatus is equipped are stored in the inventory databank. It is continuously updated and thus indicates for a respective measurement apparatus which peripherals, which technical components, which modules or other elements that are associated with the respective measurement apparatus, are currently present (for example surface coils, injectors etc.). The data from the inventory databank typically influence the measurement apparatus-specific parameters. According to one aspect of the invention, only the currently present elements of a measurement apparatus must respectively be taken into account in the framework of the control. The preparation measures can thus be inventively executed in a targeted, up-to-date and automatic manner. It can thereby be prevented that elements of a measurement apparatus that are not currently available at the respective scanner are mistakenly included in the framework of preparation measures.

According to a further aspect of the invention, it is provided that an abstract apparatus is virtually implemented on the controller for controlling the measurement apparatus, this abstract apparatus simulating the real apparatus to be controlled by exactly the same functionality (as that of the real apparatus) being provided. According to the invention, an indirect controlling of the apparatus is thus provided by the apparatus itself not being controlled, but rather the virtual apparatus that is interposed as a simulation of the real apparatus. It is thereby possible to completely decouple the preparation procedure (or the control procedure) from the measurement procedure, and both in a temporal and in a mechanical (spatial) regard. In other words, it is possible to execute preparation measures for preparation of a measurement task at an arbitrary controller. Moreover, it is possible to execute the preparation measures in a selectable time span that does not necessarily have to lie immediately before the measurement procedure. The preparation measures thus now no longer have to be implemented at a system console of the actual scanner (as was previously necessary), but rather can be executed on, for example, a laptop that can be connected to the hospital network at an arbitrary point in time. The identical functionality that the real scanner to be controlled exhibits is then provided on the laptop. The abstract MR apparatus then simulates the real MR apparatus to be controlled. The data necessary for this can be obtained by interrogating the real apparatus (for example over a network connection or via another interface). It is also possible to automatically generate the data necessary for this via a model calculation or a simulation. Data from a databank are typically used that depend on their statistical legitimacy for the respective existing boundary conditions (apparatus-specific parameters, measurement-specific parameters (for example age, size and weight of the patient) and other variables). Moreover, user interactions via a corresponding provided user interface are naturally also possible with which, for example, specific parameters can be input in relation to the real apparatus. According to one aspect of the invention, the user can select from a set of provided standard assumptions, or specific standard configurations are preset. Specific control parameters can therewith also be manually entered.

According to the invention, the actual apparatus is not controlled but rather a virtual simulation of the apparatus (as explained above). It is possible to execute the control or the control and preparation procedure entirely independently of the actual measurement in a temporal, spatial and/or other regard (for example with regard to the participating data technology resources). Not only is flexibility gained, but also the situation is prevented of an MR apparatus becoming unnecessarily busy due to preparation measures without being able to execute a measurement. These preparation measures can be inventively executed on an arbitrary computer and at any point in time before the measurement.

In an embodiment of the invention, the generated control parameters are transferred to the actual apparatus so that the apparatus can be configured, preset and/or controlled for the respective data acquisition procedure. According to the invention, the controlling of the actual apparatus does not necessarily have to ensue directly in connection with the preparation measures. The apparatus can already be prepared (configured), while a different, current measurement is ensuing on the actual apparatus. Only at a later point in time is the actual apparatus then automatically configured using the control parameters.

The user can then set at which point in time the actual measurement should be executed.

All or selected method steps of the inventive method can be executed automatically. Errors that have previously occurred due to manual generation of the control parameters thus can be avoided.

By the inventive decoupling of the control procedure from the measurement procedure it is possible for the measurement procedure to be externally controlled from arbitrary controllers. Moreover, it is possible for various measurement procedures to be controlled by a number of (different) controllers that are then sequentially executed by a single real apparatus. In the event that a number of controllers are used in order to control a measurement procedure, the respective control parameters generated on the different controllers can thus be consolidated. Furthermore, it is possible to control a number of MR apparatuses from one and the same controller. Overall an n:n relationship results between the preparation device (controller) and the actual examination apparatus.

BRIEF DESCRIPTION OF THE DRAWINGS

The single FIGURE is a schematic illustration of an embodiment of an inventive control system for an MR scanner, operable in accordance with the inventive method and data structure.

DESCRIPTION OF THE PREFERRED EMBODIMENTS

A medical technology measurement apparatus, in particular a magnetic resonance tomography apparatus 10, is typically equipped with an operator console 12 that is either directly connected to the tomography apparatus 10 or is involved in data exchange with the MR apparatus 10 via a network NW.

For preparation of a measurement (examination data acquisition) with the MR apparatus 10, it must be configured or preset. This has conventionally ensued directly at the operator console 12 of the MR apparatus 10. This disadvantageous limitation is avoided with the inventive solution. In accordance with the invention it is possible to execute the preparation measures for controlling the MR apparatus 10 on arbitrary controllers 14. The controllers 14 for controlling the MR apparatus 10 can be servers, laptops or other workstations that are schematically depicted on the right side of the FIGURE. It is also possible to have the control tasks executed from multiple controllers 14. One controller 14 can likewise control a number of MR apparatuses 10.

In the method for controlling the MR apparatus 10, namely for preparation of a measurement procedure, a databank DB is accessed in which are stored data and parameters that are relevant for the control and/or preparation of the MR apparatus 10. These data are advantageously measurement apparatus-specific parameters and/or examination-specific parameters (that thus concern the actual measurement procedure). A virtual MR apparatus 16 that simulates the actual real MR apparatus 10 is implemented on the controller 14 for controlling the MR apparatus 10. This is illustrates in the FIGURE by an abstract virtual apparatus 16, which is designed for control of the MR apparatus 10, depicted above the bracket for all controllers 14.

The controller 14 is not the operator console 12 of the real scanner 10 but rather is, for example, a workstation or a laptop that is/are connected with the further modules via a network. A functionality that exactly corresponds to the functionality of the real scanner 10 is provided to the user via the virtual apparatus 16. Via a user interface of the controller 14, a user can enter data that are relevant to the control of the MR apparatus 10, but the user communicates only with the virtual apparatus 16 and not with the real scanner 10.

The virtual apparatus 16 is fashioned such that the parameters relevant for the control are automatically requested. The relevant parameters can be entered by the user via a user interface and/or can be imported via the network NW (for example from the databank DB) or can be derived from further connected modules that execute a model calculation for controlling the scanner 10. All necessary parameters (system parameters, application-specific parameters and measurement-specific parameters) are automatically requested by the virtual apparatus 16. The relevant data can be also optionally already stored on the controller 14. In an embodiment of the invention, the provision of the relevant parameters largely ensues transparently for the user. User interaction occurs only in the event that it is necessary. For example, a user interface that allows the user to make a selection that designates which or how many surface coils are actually required or should be provided for the measurement to be controlled. According to one aspect of the invention, all parameters are preconfigured.

After all relevant parameters have been imported and registered, these are translated into control parameters. The control parameters serve to control the MR scanner 10. The data set with the control parameters can be automatically related to the real MR scanner 10 (for example via the network NW) for execution. In this case the MR scanner 10 is directly and immediately configured using the control parameters. As an alternative to this it is also possible for the data set with the control parameters to be stored or saved in the system and to be transferred to the MR scanner 10 for execution at a configurable (later) point in time. The inventive system thus can be variably designed in terms of the time at which the transfer occurs.

After the control parameters have been imported by the MR scanner 10, the MR scanner 10 is automatically configured or set in order to then be able to implement the intended measurement.

Since the virtual apparatus 16 and the respective underlying infrastructure layers (query of the system parameters via the network NW, simulations and model assumptions etc.) optimally reproduce the real measurement environment, only a few adjustments at the real apparatus 10 itself are still necessary (if at all) that moreover can be executed in a wholly automated manner using already-existing techniques such as, for example, auto-align techniques. The conventional procedures known in the prior art for automatic preparation and control of a measurement apparatus 10 thus can also be integrated into the inventive system. Further adjustments at the real magnetic resonance apparatus 10 are then no longer necessary since they have all already been executed through the virtual apparatus 16 and the controller 14.

Due the provision of a virtual apparatus 16 at the controller 14, the procedure for setting the control is in principle independent of the technical configuration or design of the respective controller 14. It is even possible for a real scanner 10 that is not associated with the respective operator console 12 to be controlled from the operator console 12 that acts as a controller 14. In other words, a "foreign" MR apparatus 10 can be controlled from an operator console 12 functioning as a controller 14 for the "foreign" MR apparatus 10.

The preparation of a measurement and/or the controlling of a measurement task can be decoupled from the actual measurement task in accordance with the invention. The real MR scanner 10 (which can be designated as a "target apparatus)" is therefore simulated in the abstract as a virtual apparatus 16 on an arbitrary controller 14. The control and/or preparation thus can be executed on a device that is independent of the target apparatus.

The abstract (virtual) apparatus 16 can either directly access the target apparatus (in particular when the controller 14 for controlling the apparatus 10 is the corresponding operator console 12 of the respective apparatus 10 and thus the data are locally available) or it can request the relevant data and parameters over a network connection. Moreover, the parameters can also be provided in the manner of a model calculation or simulation.

In an embodiment of the invention the generated control parameters are compared with reference control parameters that are stored in the databank DB. If inconsistencies are noted, the user should verify the respective specifications via a user interface. If, f If, for example, for a specific scanner 10 and a specific measurement, the reference data refer to a predetermined number of RF reception channels, shim channels etc. that deviates from registered apparatus-specific parameters, the user is informed of this inconsistency and can select the valid parameters according to a pre-selection and thus avoid a possible error. The system can also be easily expanded in that additional modules can be easily added by a corresponding entry into the databank DB.

The virtual apparatus 16 advantageously has a user interface, a connection to the network NW for access to remote modules and possibly an interface to the real apparatus 10 (in particular when the controller 14 is the operator console 12 of the real scanner 10). For control, the virtual apparatus 16 either relays required information to a system databank via the network NW or it directly communicates these queries to the real apparatus 10. Moreover, such queries can also be registered via a provided user interface.

For example, suitable coil elements that must be individually aligned on the patient and arranged must be selected for an MR measurement. Only precisely those coils which are also actually, currently "plugged" into the MR apparatus 10 (together with the patient), or are connected with the MR apparatus 10 at this moment can be available for selection for this purpose. In conventional methods this information was available only locally, and not to another computer. However, according to the invention this information can also be accessed by every arbitrary computer (also using the mentioned coil simulation program). The user that can effectively virtually plug in coils on a specifically generated user interface which then receives the planning preparation communicated as plugged-in coils by means of the "abstract MR apparatus".

The basis of the inventive method is described in the following using the system parameter "transmitter reference amplitude" as a further example in addition to the coil simulation program mentioned in the preceding.

Among other things, the individual system parameter "transmitter reference amplitude" (TraRefAmpl) is required for every single imaging MR examination. This parameter must be determined for every patient, among other things for every different position of the patient relative to the MR scanner 10. At the same time this parameter has influence on other parameters in the planning of the measurement task (interdependencies or secondary effects). By means of a mathematical model of the patient (dependent on age, size and weight), the parameter TraRefAmpl can be predicted well, for example also for the purposes of a measurement task planning (for example in comparison to a random assumed number). This algorithm can be implemented in the inventive method by means of a computer program.

The description of the invention and the exemplary embodiments are non-limiting with regard to any specific physical realization of the invention. For those skilled in the art it is clear that the invention can be realized partially or entirely in software and/or hardware and/or distributed among a number of physical products (in particular computer program products).

Although modifications and changes may be suggested by those skilled in the art, it is the intention of the inventor to embody within the patent warranted hereon all changes and modifications as reasonably and properly come within the scope of his contribution to the art.

I claim:

1. A method for controlling an actual medical imaging apparatus installed at an installation site and having a manually operable apparatus control unit connected to the actual medical imaging apparatus at said installation site, said actual medical imaging apparatus being configured to operate by executing a set of apparatus functions to generate medical image data, said method comprising the steps of:

at a controller that is independent of said actual medical imaging apparatus and said apparatus control unit, accessing an electronically generated virtual representation of said actual medical imaging apparatus that simulates execution of said set of apparatus functions;

for a medical image data acquisition procedure using said actual medical imaging apparatus, accessing, from said controller, at least one accessed parameter selected from the group consisting of parameters specific to said procedure and parameters specific to said actual medical imaging apparatus;

in said controller, generating setting parameters for setting said actual medical imaging apparatus to execute said medical data acquisition procedure, by applying said at least one accessed parameter to said virtual representation and simulating said set of apparatus functions with said virtual representation according to said at least one accessed parameter; and communicating said setting parameters from said controller to said apparatus control unit at said installation site, and operating said actual medical imaging apparatus to execute said medical image data acquisition procedure according to said setting parameters with no manual entry of said setting parameters at said apparatus control unit.

2. A method as claimed in claim 1 comprising storing all information necessary for operation of said medical imaging apparatus in a databank, and accessing said databank from said controller, as needed, to generate said setting parameters using said at least one accessed parameter in combination with said information from said databank.

3. A method as claimed in claim 1 comprising temporally and spatially decoupling said controller from said measurement procedure.

4. A method as claimed in claim 1 comprising accessing said at least one accessed parameter via a user interface in communication with said controller.

5. A method as claimed in claim 1 comprising accessing said at least one accessed parameter as at least one preset parameter generated from a model calculation based on said medical imaging apparatus.

6. A method as claimed in claim 5 comprising generating said at least one preset parameter using a model calculation based on said medical imaging apparatus with the patient therein.

7. A medical imaging system comprising:
- an actual medical imaging apparatus installed at an installation site and having a manually operable apparatus control unit connected to the actual medical imaging apparatus at said installation site, said actual medical imaging apparatus being configured to operate by executing a set of apparatus functions to generate medical image data;
- a controller that is independent of said actual medical imaging apparatus and said apparatus control unit, said controller being configured to access an electronically generated virtual representation of said actual medical imaging apparatus that simulates execution of said set of apparatus functions;
- for a medical image data acquisition procedure using said actual medical imaging apparatus, said controller being configured to access at least one accessed parameter selected from the group consisting of parameters specific to said procedure and parameters specific to said actual medical imaging apparatus;
- said controller being configured to automatically generate setting parameters for setting said actual medical imaging apparatus to execute said medical data acquisition procedure, by applying said at least one accessed parameter to said virtual representation and simulating said set of apparatus functions with said virtual representation according to said at least one accessed parameter; and
- said controller communicating said setting parameters from said controller to said apparatus control unit at said installation site, and said apparatus control unit being configured to operate said actual medical imaging apparatus to execute said medical image data acquisition procedure according to said setting parameters with no manual entry of said setting parameters at said apparatus control unit.

8. A non-transitory computer-readable medium encoded with programming instructions for operating a controller to generate setting parameters for an actual medical imaging apparatus installed at an installation site, said actual medical imaging apparatus having a manually operable apparatus control unit connected to the actual medical imaging apparatus at said installation site and said controller being independent of said actual medical imaging apparatus and said apparatus control unit, said actual medical imaging apparatus being configured to operate by executing a set of apparatus functions to generate medical image data, said programming instructions causing said controller to:
- access an electronically generated virtual representation of said actual medical imaging apparatus that simulates execution of said set of apparatus functions;
- for a medical image data acquisition procedure using said actual medical imaging apparatus, access at least one accessed parameter selected from the group consisting of parameters specific to said procedure and parameters specific to said actual medical imaging apparatus;
- generate setting parameters for setting said actual medical imaging apparatus to execute said medical data acquisition procedure, by applying said at least one accessed parameter to said virtual representation and simulating said set of apparatus functions with said virtual representation according to said at least one accessed parameter; and
- communicate said setting parameters from said controller to said apparatus control unit at said installation site in a form allowing said apparatus control unit to operate said actual medical imaging apparatus to execute said medical image data acquisition procedure according to said setting parameters with no manual entry of said setting parameters at said apparatus control unit.

* * * * *